(12) United States Patent
Palmer et al.

(10) Patent No.: US 8,919,452 B2
(45) Date of Patent: Dec. 30, 2014

(54) CASING SPEARS AND RELATED SYSTEMS AND METHODS

(75) Inventors: Larry T. Palmer, Spring, TX (US); Dennis E. Kroll, League City, TX (US); Gregory L. Hern, Porter, TX (US)

(73) Assignee: Baker Hughes Incorporated, Houston, TX (US)

( * ) Notice: Subject to any disclaimer, the term of this patent is extended or adjusted under 35 U.S.C. 154(b) by 519 days.

(21) Appl. No.: 13/280,113

(22) Filed: Oct. 24, 2011

(65) Prior Publication Data

US 2012/0111556 A1    May 10, 2012

Related U.S. Application Data

(60) Provisional application No. 61/411,195, filed on Nov. 8, 2010.

(51) Int. Cl.
  *E21B 19/10* (2006.01)
  *E21B 19/06* (2006.01)

(52) U.S. Cl.
  CPC ..................................... *E21B 19/06* (2013.01)
  USPC .......................................... 166/381; 175/423

(58) Field of Classification Search
  CPC ....................................................... E21B 19/10
  USPC .................................. 166/373, 381; 175/423
  See application file for complete search history.

(56) References Cited

U.S. PATENT DOCUMENTS

| | | | |
|---|---|---|---|
| 1,825,026 A * | 9/1931 | Thomas ....................... | 294/86.19 |
| 2,134,749 A * | 11/1938 | Burt ................................ | 29/413 |
| 2,671,514 A | 3/1954 | Haines | |
| 2,720,267 A * | 10/1955 | Brown .......................... | 166/119 |
| 3,283,824 A | 11/1966 | Hoffman et al. | |
| 3,412,800 A | 11/1968 | Kesling, III | |
| 3,603,388 A * | 9/1971 | Current et al. ................ | 166/120 |
| 3,727,967 A | 4/1973 | Anastasiu et al. | |
| 4,311,196 A * | 1/1982 | Beall et al. ..................... | 166/134 |

(Continued)

FOREIGN PATENT DOCUMENTS

| | | |
|---|---|---|
| JP | 09060468 | 3/1997 |
| JP | 2009018214 | 1/2009 |
| WO | 2007019594 | 2/2007 |

OTHER PUBLICATIONS

Baker Hughes Incorporated, Technical Unit 4614, Type D Casing Spear, Product Family No. H12009, Oct. 2010, 2 pages.

(Continued)

*Primary Examiner* — Cathleen Hutchins
(74) *Attorney, Agent, or Firm* — Steve Rosenblatt (57) ABSTRACT

A casing spear may comprise a mandrel, and a slip assembly comprising at least one slip. The at least one slip may comprise a generally wedge-shaped surface positioned and configured to cause the at least one slip to move radially outwards relative to the mandrel in response to a rotation of the mandrel and a torque acting on the slip assembly, the torque opposing the rotation of the mandrel. Additionally, a method of operating a casing spear may comprise inserting a casing spear into a casing, rotating a mandrel of the casing spear, applying a torque to a slip assembly of the casing spear with the casing, opposing the rotation of the mandrel, and applying a force in a radial direction to at least one slip of a slip assembly of the casing spear in response to the torque.

30 Claims, 10 Drawing Sheets

(56) References Cited

U.S. PATENT DOCUMENTS

| | | | |
|---|---|---|---|
| 4,844,154 | A * | 7/1989 | Ross et al. .................. 166/139 |
| 5,045,832 | A | 9/1991 | Tam |
| 5,265,937 | A | 11/1993 | Allen |
| 5,623,991 | A | 4/1997 | Jani |
| 5,771,970 | A | 6/1998 | Jani |
| 5,971,079 | A | 10/1999 | Mullins |
| 6,062,309 | A | 5/2000 | Gosse |
| 6,155,346 | A | 12/2000 | Aldridge |
| 6,199,641 | B1 | 3/2001 | Downie et al. |
| 6,227,306 | B1 | 5/2001 | Downie et al. |
| 6,309,002 | B1 | 10/2001 | Bouligny |
| 6,311,792 | B1 | 11/2001 | Scott et al. |
| 6,318,459 | B1 | 11/2001 | Wright et al. |
| 6,536,520 | B1 | 3/2003 | Snider et al. |
| 6,550,540 | B2 | 4/2003 | Trent |
| 6,688,394 | B1 | 2/2004 | Ayling |
| 6,688,398 | B2 | 2/2004 | Pietras |
| 6,705,413 | B1 | 3/2004 | Tessari |
| 6,725,938 | B1 | 4/2004 | Pietras |
| 6,732,822 | B2 | 5/2004 | Slack et al. |
| 6,742,584 | B1 | 6/2004 | Appleton |
| 7,021,374 | B2 | 4/2006 | Pietras |
| 7,021,382 | B2 | 4/2006 | Angman et al. |
| 7,044,241 | B2 | 5/2006 | Angman |
| 7,077,205 | B2 | 7/2006 | Eddison |
| 7,107,875 | B2 | 9/2006 | Haugen et al. |
| 7,117,957 | B2 | 10/2006 | Metcalfe et al. |
| 7,121,350 | B2 | 10/2006 | Aldridge et al. |
| 7,137,454 | B2 | 11/2006 | Pietras |
| 7,140,443 | B2 | 11/2006 | Beierbach et al. |
| 7,140,445 | B2 | 11/2006 | Shahin et al. |
| 7,165,609 | B2 | 1/2007 | Slack et al. |
| 7,191,840 | B2 | 3/2007 | Pietras et al. |
| 7,219,744 | B2 | 5/2007 | Pietras |
| 7,325,610 | B2 | 2/2008 | Giroux et al. |
| 7,334,650 | B2 | 2/2008 | Giroux et al. |
| 7,360,594 | B2 | 4/2008 | Giroux et al. |
| 7,370,707 | B2 | 5/2008 | McDaniel et al. |
| 7,377,324 | B2 | 5/2008 | Beierbach et al. |
| 7,475,742 | B2 | 1/2009 | Angman et al. |
| 7,513,300 | B2 | 4/2009 | Pietras et al. |
| 7,624,820 | B2 | 12/2009 | Angman et al. |
| 7,647,990 | B2 | 1/2010 | Tessari et al. |
| 7,654,325 | B2 | 2/2010 | Giroux et al. |
| 7,654,334 | B2 | 2/2010 | Manson |
| 7,673,675 | B2 | 3/2010 | Carr et al. |
| 7,681,649 | B2 | 3/2010 | Cerovsek |
| 7,694,730 | B2 | 4/2010 | Angman |
| 7,712,523 | B2 | 5/2010 | Snider et al. |
| 7,757,754 | B2 | 7/2010 | McKay |
| 7,770,635 | B2 | 8/2010 | Angman |
| 7,784,551 | B2 | 8/2010 | Angman et al. |
| 7,874,352 | B2 | 1/2011 | Odell et al. |
| 7,896,111 | B2 | 3/2011 | Slack |
| 7,909,120 | B2 | 3/2011 | Slack |
| 2002/0170720 | A1 | 11/2002 | Haugen |
| 2004/0216892 | A1 | 11/2004 | Giroux et al. |
| 2005/0000691 | A1 | 1/2005 | Giroux et al. |
| 2005/0269105 | A1 | 12/2005 | Pietras |
| 2007/0074876 | A1 | 4/2007 | Pietras |
| 2007/0131416 | A1 | 6/2007 | Odell et al. |
| 2007/0193751 | A1 | 8/2007 | Pietras et al. |
| 2008/0083540 | A1 | 4/2008 | Haugen |
| 2008/0210439 | A1 | 9/2008 | Angman et al. |
| 2008/0302525 | A1 | 12/2008 | Beierbach et al. |
| 2009/0101332 | A1 | 4/2009 | Shahin et al. |
| 2009/0120649 | A1 | 5/2009 | Cerovesek |
| 2009/0126936 | A1 | 5/2009 | Begley et al. |
| 2009/0126941 | A1 | 5/2009 | Laitolais, Jr. et al. |
| 2009/0136326 | A1 | 5/2009 | Angman |
| 2009/0242192 | A1 | 10/2009 | Jensen et al. |
| 2009/0272543 | A1 | 11/2009 | Bouligny et al. |
| 2009/0314496 | A1 | 12/2009 | Begnaud et al. |
| 2009/0321086 | A1 | 12/2009 | Zimmermann |
| 2010/0139978 | A9 | 6/2010 | Giroux et al. |
| 2010/0155052 | A1 | 6/2010 | Manson |

OTHER PUBLICATIONS

Baker Hughes Incorporated, Technical Unit 4607, Type B Casing Spear, Product Family No. H12609, Nov. 2010, 2 pages.

Baker Hughes Incorporated, Technical Unit 4160, Model B-2 and B-3 Tubing Anchor Catcher, Product Family Nos. H69803 and H69804, Oct. 2003, 3 pages.

Tesco, Casing Drive System, Bulletin 41000e, www.tescocorp.com, Jun. 2005, 4 pages.

* cited by examiner

FIG. 10

CASING SPEARS AND RELATED SYSTEMS AND METHODS

CROSS REFERENCE TO RELATED APPLICATION

This application is claims priority from U.S. Provisional Patent Application Ser. No. 61/411,195 for "Casing Spears and Related Systems and Methods, filed on Nov. 8, 2010, the disclosure of which is incorporated herein by reference in its entirety.

FIELD OF THE INVENTION

Embodiments of the present invention relate to manipulating casing for subterranean well bores. More particularly, embodiments of the present invention relate to methods and apparatus for gripping and rotating casing by the interior thereof from the earth's surface, which methods and apparatus may be employed to drill or ream with casing.

BACKGROUND OF THE INVENTION

It is known in the art of subterranean drilling to use a so-called "top drive" to connect a section, also known as a "joint," of well bore casing above a drilling rig floor to the upper end of a casing string substantially disposed in the well bore. Such casing strings, commonly termed "surface casing," may be set into the well bore as much as 3,000 feet (914.4 meters), and typically about 1,500 feet (457.2 meters), from the surface.

Examples of methods and apparatus for making casing joint connections to a casing string are disclosed in U.S. Pat. Nos. 6,742,584 and 7,137,454, the disclosure of each of which patents is incorporated herein by this reference.

It is known in the art of subterranean drilling to drill and ream with casing, using a drilling or reaming shoe including a cutting structure thereon to drill a well bore, or to ream an existing well bore to a larger diameter, to remove irregularities in the well bore, or both. It would be highly desirable for the subterranean drilling industry to employ a top drive to apply weight on the casing in combination with casing rotation to drill or ream with casing using a drilling or reaming device at the distal end of the casing string. Additionally, improved casing spears for such applications would be desirable.

SUMMARY OF THE INVENTION

In one embodiment, a casing spear may comprise a mandrel, and a slip assembly comprising at least one slip. The at least one slip may comprise a generally wedge-shaped surface positioned and configured to cause the at least one slip to move radially outwards relative to the mandrel in response to a rotation of the mandrel and a torque acting on the slip assembly, the torque opposing the rotation of the mandrel.

In another embodiment, a method of operating a casing spear may comprise inserting a casing spear into a casing, rotating a mandrel of the casing spear, applying a torque to a slip assembly of the casing spear with the casing, opposing the rotation of the mandrel, and applying a force in a radial direction to at least one slip of a slip assembly of the casing spear in response to the torque.

DETAILED DESCRIPTION OF THE PREFERRED EMBODIMENT

The illustrations presented herein are not actual views of any particular drilling system, assembly, or device, but are merely idealized representations which are employed to describe embodiments of the present invention.

While embodiments of the present disclosure are described herein with respect to manipulation of, and drilling with, casing, it is also contemplated that an appropriately sized drive assembly may be used to engage, rotate, and apply weight for drilling with any suitable tubular goods having sufficient longitudinal compressive and torsional (shear) strength to withstand application of longitudinal force and torque for drilling. Accordingly, as used herein, the term "casing" means and includes not only convention casing joints but also liner joints, drill pipe joints, and drill collar joints. In addition, multiple joint assemblies, termed "stands," of any and all of the foregoing tubular goods may be used with, and manipulated by, embodiments of the apparatus of the present disclosure and in accordance with methods of the present disclosure.

As used herein, the terms "upper," "lower," "above," and "below," are used for the sake of clarity in a relative sense as an embodiment of the casing drive assembly is oriented during use to manipulate and drive a casing joint or string.

In some embodiments, such as is shown in the preferred embodiment of FIGS. 1A-1D, a casing spear 10 may comprise a mandrel 12, a circumferential stop collar 14, a slip assembly 16, and a drag block assembly 18. Additionally, the casing spear 10 may include a cup type packer, such as cup type packer 120 shown in FIGS. 4A-4D. The mandrel 12 may include a longitudinal fluid passage 20 (FIGS. 1B and 1D) extending therethrough and include a retention ring 22 (FIGS. 1B and 1D) extending radially outward. The circumferential stop collar 14 may be coupled to a spacing sleeve 24 and the spacing sleeve 24 may be coupled to an upper sub 26 of the slip assembly 16, such as by interlocking threads. The upper sub 26 and the spacing sleeve 24 may be positioned on either side of the retention ring 22 of the mandrel 12, such that the retention ring 22 may prevent the longitudinal movement of the upper sub 26 and the spacing sleeve 24 relative to the mandrel 12. Likewise, the spacing sleeve 24 may prevent the longitudinal movement of the circumferential stop collar 14 relative to the mandrel 12.

The slip assembly 16 may include a plurality of slips 28, the upper sub 26 and a lower sub 30. Each of the upper sub 26 and the lower sub 30 may include slots 32 (FIGS. 1A and 1C) configured to receive a tail piece 34 of a corresponding slip 28. The tail piece 34 of each slip 28 may be inserted into a slot 32 of one of the upper sub 26 and lower sub 30 and slidably coupled thereto.

Figure 2:
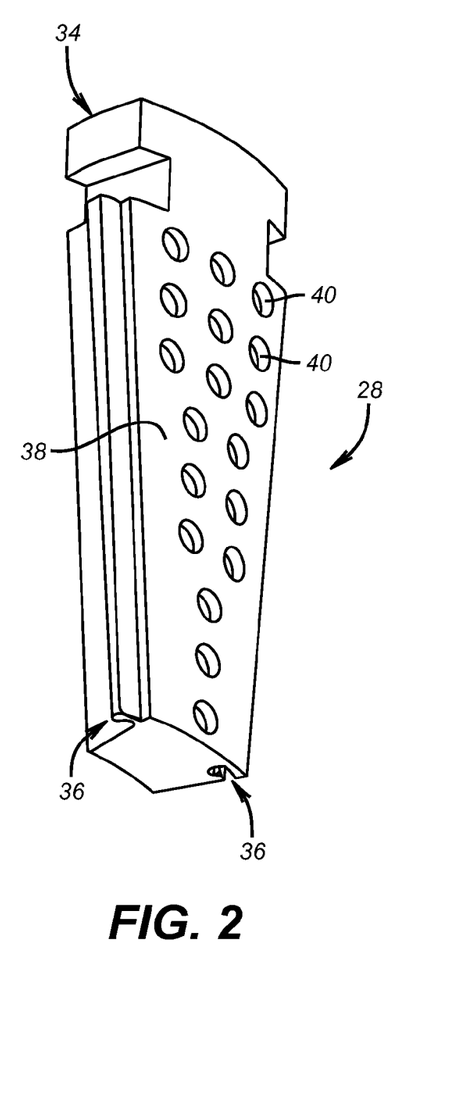
FIG. 2 is an isometric view of a slip for a casing spear, such as shown in FIG. 1A.
Figure 5:
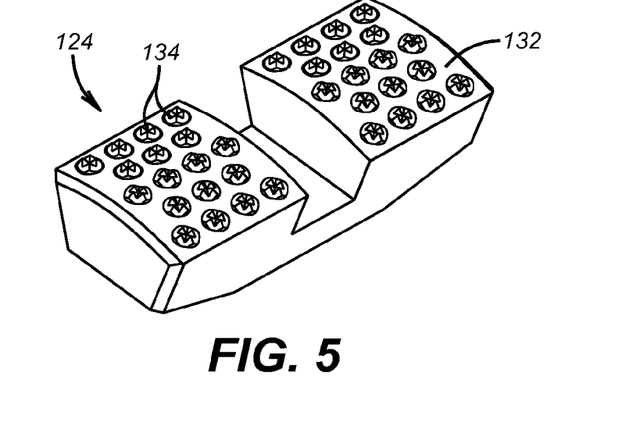
FIG. 5 is an isometric view of a slip for a casing spear, such as shown in FIG. 4A, including carbide inserts.
Figure 6:
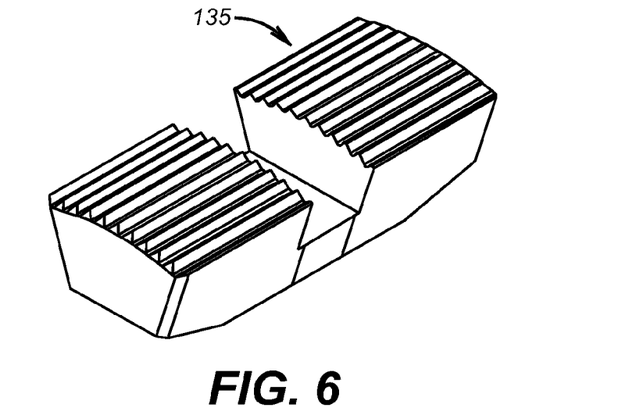
FIG. 6 is an isometric view of a slip for a casing spear, such as shown in FIG. 4A, including wickers.
Figure 7:
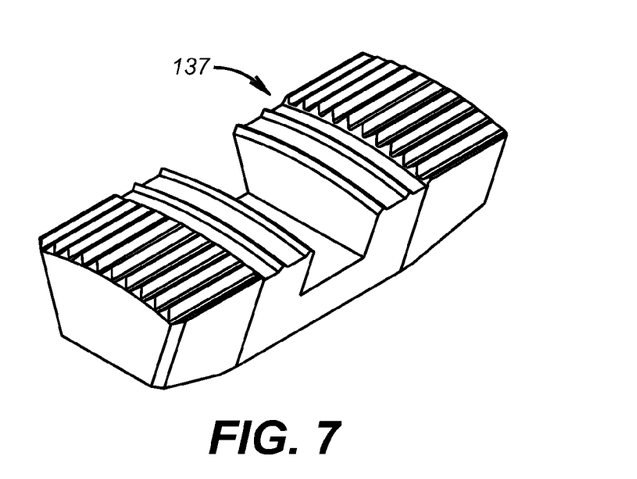
FIG. 7 is an isometric view of a slip for a casing spear, such as shown in FIG. 4A, including wickers in an additional configuration.

Each slip 28 (as shown in isometric view in FIG. 2) may also include interlocking features 36 to slidably couple each slip 28 to slips 28 circumferentially adjacent thereto. In view of this, each slip 28 may be slidable in a radial direction relative to the upper sub 26 and the lower sub 30, and the slips 28 coupled to the lower sub 30 may be slidable in an axial direction relative to the slips 28 coupled to the upper sub 26. Each slip 28 may also have a general wedge shape in the region of the interlocking features 36 wherein the slips 28 are slidably coupled to adjacent slips 28, such that as the tail pieces 34 of the slips 28 are moved closer together, the slips 28 may be urged radially outwards. The outer surfaces 38 of the slips 28 may comprise gripping structures. Such gripping structures may comprise, by way of example, machined teeth, wickers (such as are shown in FIGS. 6 and 7), crushed tungsten carbide, tungsten carbide inserts in the form of bricks, buttons or discs (such as are shown in FIG. 5) inserted into pockets 40, superabrasive elements such as natural or polycrystalline diamond, or a combination thereof. In one embodiment, such as shown in FIG. 5, the gripping structures comprise tungsten carbide inserts in the form of buttons having four projecting, pyramidal points. In additional embodiments, the gripping structures may be wickers, such as shown in FIGS. 6 and 7, which may be oriented in an axial direction, a circumferential direction, another direction or a combination thereof.

Figure 1A:
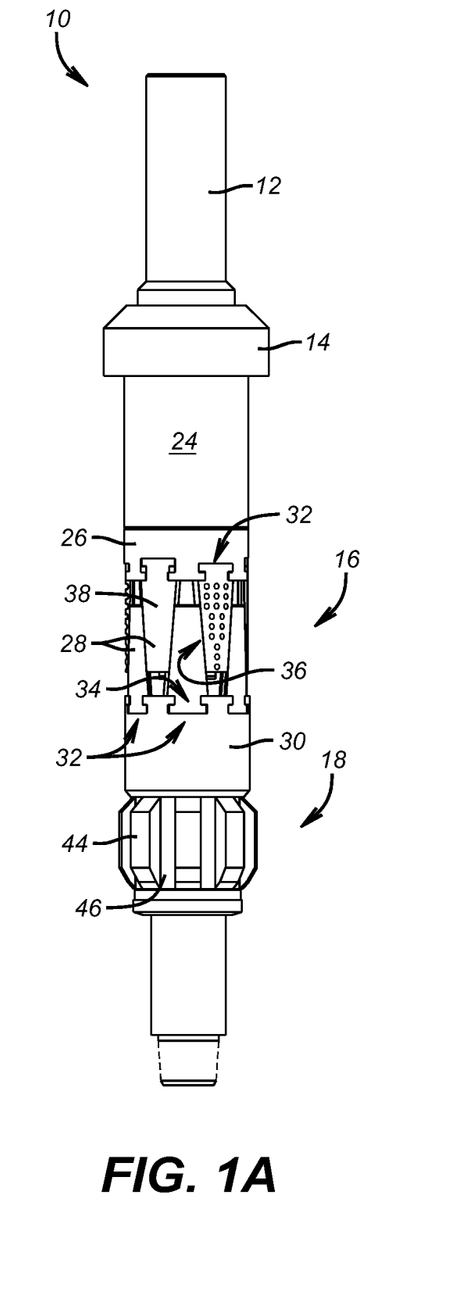
FIG. 1A is an elevation of a casing spear, according to an embodiment of the present invention, in a run-in position.
Figure 1B:
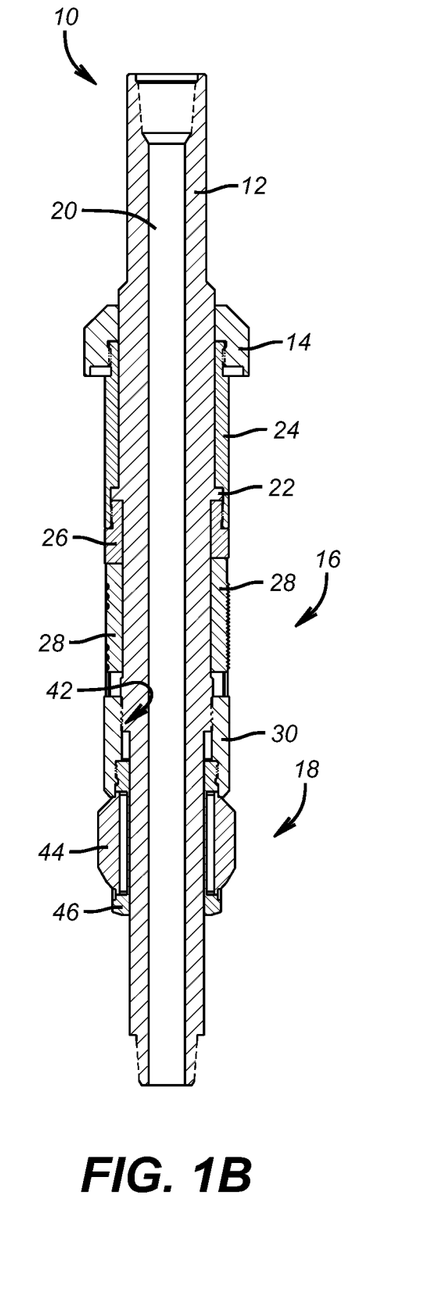
FIG. 1B is a cross-sectional view of the casing spear of FIG. 1A, in the run in position.
Figure 1C:
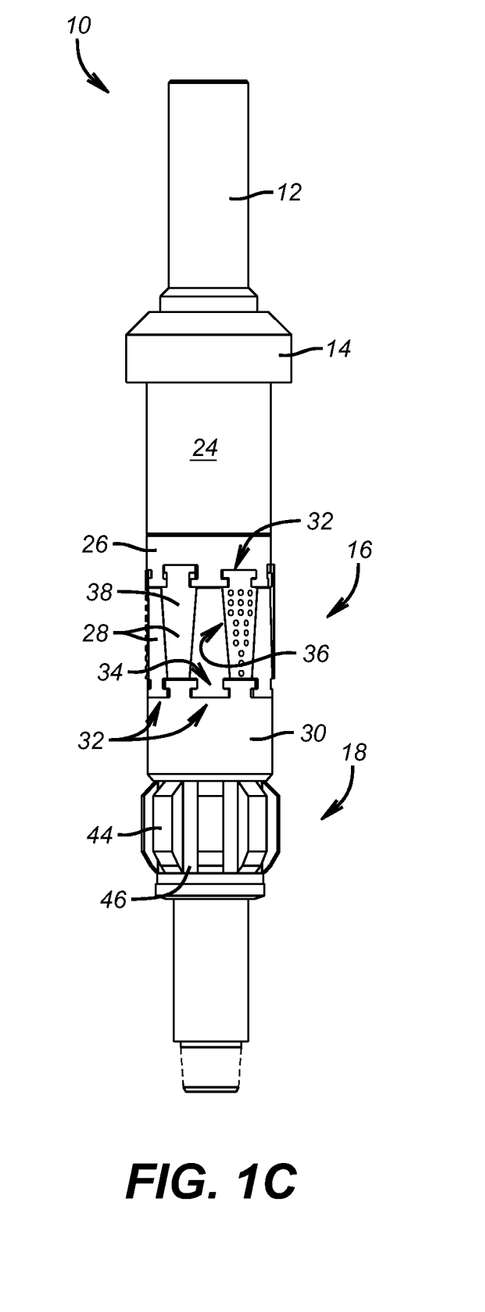
FIG. 1C is an elevation of the casing spear of FIG. 1A in a set position.
Figure 1D:
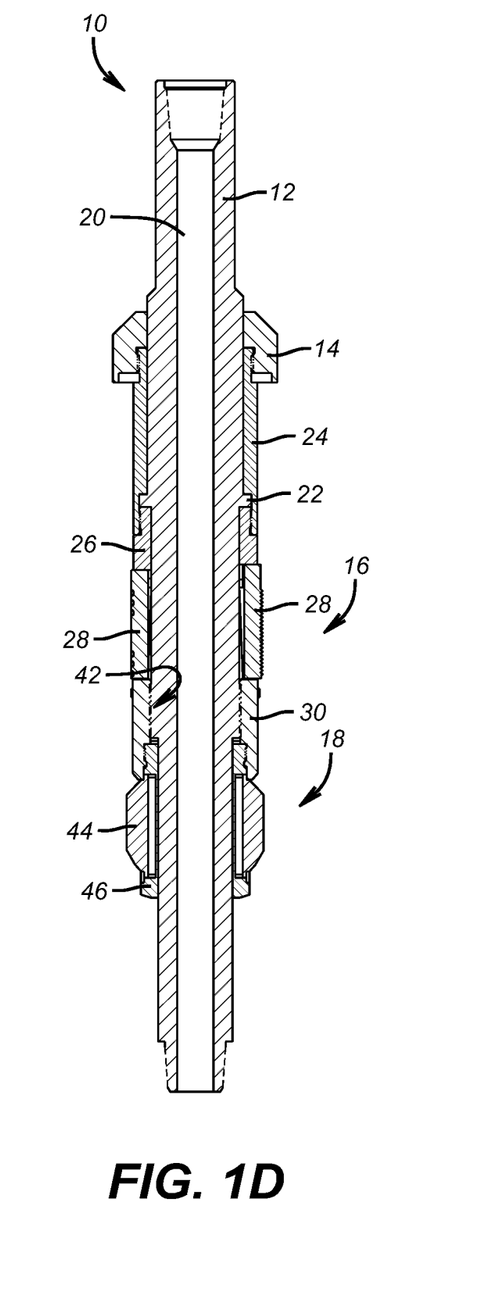
FIG. 1D is a cross-sectional view of the casing spear of FIG. 1A, in the set position.

As shown in FIGS. 1B and 1D, the lower sub 30 may include a threaded region 42 mated with corresponding threads on the outer surface of the mandrel 12. Additionally, the lower sub 30 may be fixedly coupled to the drag block assembly 18. The drag block assembly 18 may include a plurality of drag blocks 44 circumferentially distributed within a frame 46, and the drag blocks 44 may be biased radially outward, such as by helical compression springs.

Figure 3:
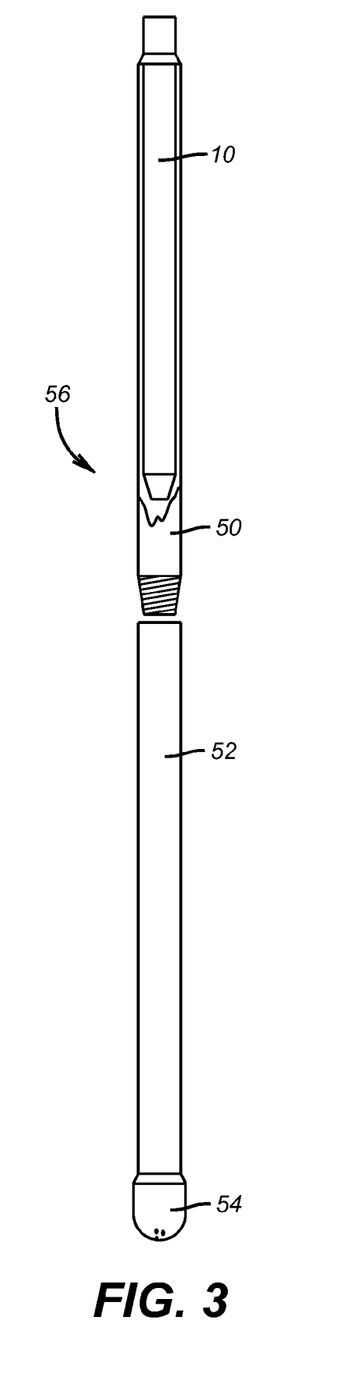
FIG. 3 is a schematic of a casing spear, such as shown in FIG. 1A, disposed within a casing joint of a casing string above another casing joint.

In use, and with reference to drawing FIG. 3, wherein a casing joint 50 is shown disposed above another casing joint 52, a single joint of casing is picked up using rig elevators, as is conventional, and stabbed up into an existing casing joint (if a casing string has already been started). A casing spear 10 in a run-in position, such as shown in FIGS. 1A and 1B, is made up with and suspended from a top drive via a slack joint, and lowered by the top drive into the bore of the casing joint 50 from the top thereof. The elevators stay latched and ride down the casing joint 50 during this operation.

If a casing joint is the first joint in the casing string, a cutting structure, such as a drilling or reaming device, is made up with the lower end thereof prior to insertion of casing spear 10. Examples of such devices are, for drilling, the EZ Case™ casing bit and, for reaming, the EZ Ream™ shoe, each of which is commercially available from the assignee of the present disclosure. Otherwise, such a device 54 is already secured to the distal end of the lowermost casing joint 52 in the casing string 56.

Upon insertion of the casing spear 10 into the casing joint 50, one or more pumps associated with the drilling rig may be engaged, and circulation of drilling fluid, also known as "mud," established through the casing drive assembly 10 through the longitudinal passage 20 of the mandrel 12 and out into the interior of the casing joint 50. Upward circulation of drilling fluid within the casing joint 50 may be precluded by a packer cup (such as packer cup 120 shown in FIGS. 4A-4D), which expands against and seals with the interior of the casing joint 50 under drilling fluid pressure.

The casing spear 10 may then be rotated, such as in a right-hand direction (i.e., clockwise looking down into the borehole). Friction between the drag blocks 44 and an inner surface of the casing 50 may be used to apply a torque to the drag block assembly 18. The torque acting on the drag block assembly 18 will also act on the lower sub 30, which is coupled to the drag block assembly 18. The torque on the lower sub 30 will cause the lower sub to rotate relative to the mandrel 12 at the threaded connection therebetween. Upon rotation, the threads will guide the lower sub 30 upwards, toward the upper sub 26. Optionally the upper sub 26 can be driven toward or away from lower sub 30 with an opposite hand threaded connection to the mandrel 12.

As the lower sub 30 is moved closer to the upper sub 26, the slips 28 will intermesh and each slip 28 will slide axially toward the slips 28 adjacent thereto. The general wedge shape of the slips 28 will cause the slips 28 to be urged radially outwards as the lower sub 30 moves upwards, toward the upper sub 26. When the slips 28 have been urged sufficiently radially outwards to a set position, such as shown in FIGS. 1C and 1D, the gripping structures of the slips 28 may grip the inner surface of the casing joint 50, and the torsion applied to the mandrel 12 may be applied to the casing through the slips.

The casing spear 10, with the casing joint 50 secured thereto, is then rotated by the top drive (the top drive also being used to provide an axial force, which is commonly termed "weight") to rotate the casing joint 50 and any others therebelow (if any) in the casing string and drilling, reaming, or another downhole operation commences. Notably, both torque and weight are applied to the casing joint 50 via engagement of the casing spear 10 substantially only with the interior of the casing joint 50.

The rig elevators remain attached as the casing joint 50 descends until a point just above the rig floor. To remove the casing spear 10, the mandrel 12 may be rotated in the opposite direction, such as in a left-hand direction (i.e., counter-clockwise looking down into the borehole), which may cause the lower sub 30 to be forced axially downward, away from the upper sub 26. As the lower sub 30 is moved axially away from the upper sub 30, the slips 28 may retract axially toward the mandrel 12 and returned to the run-in position, as shown in FIGS. 1A and 1B. Then, the casing spear 10 may be removed from the casing 50 for subsequent insertion into another casing joint 50 picked up by the rig elevators, and the above-described process may then be repeated.

In an additional embodiment, as shown in FIGS. 4A-4D, a casing spear 100 may comprise a mandrel 112, a circumferential stop collar 114, a slip assembly 116, a drag block assembly 118 and a cup type packer 120. The mandrel may include a longitudinal fluid passage 122 (FIGS. 4B and 4D) extending therethrough and may be coupled to an assembly that includes the loosely mounted cup type packer 120, such as by a threaded connection. Additionally, the circumferential stop collar 114 may be coupled to the mandrel 112 such that the stop collar 114 may be prevented from axial movement relative to the mandrel 112.

Figure 4A:
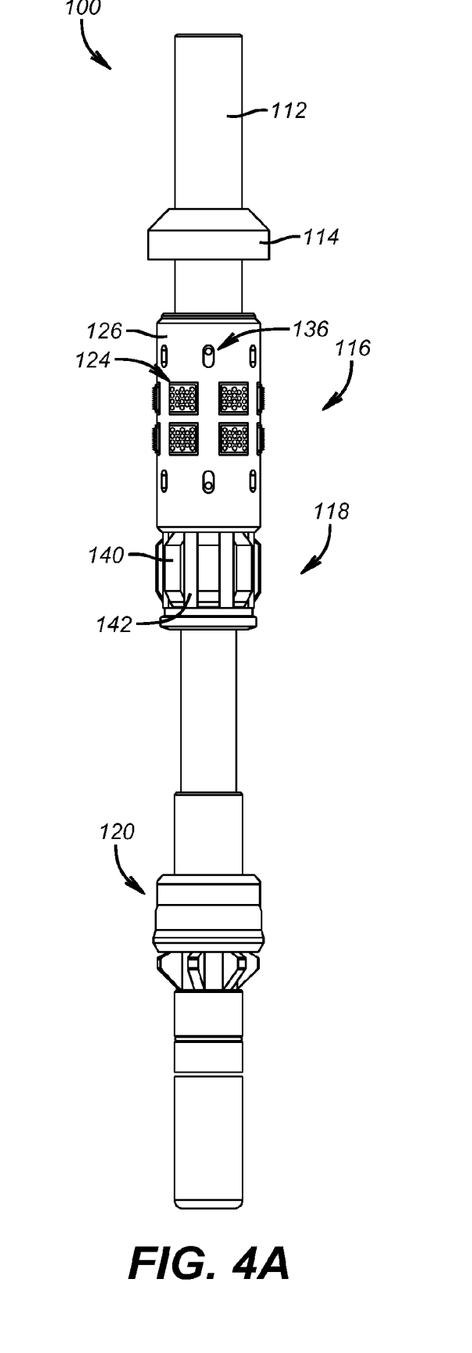
FIG. 4A is an elevation of a casing spear, according to an additional embodiment of the present invention, in a run-in position.
Figure 4B:
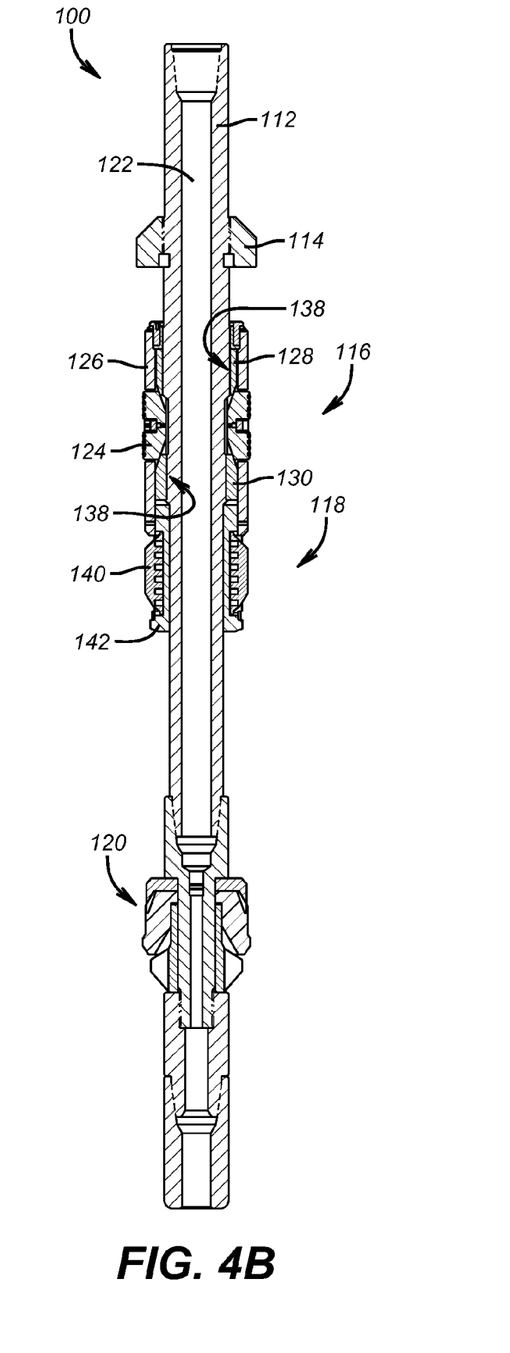
FIG. 4B is a cross-sectional view of the casing spear of FIG. 4A, in the run in position.
Figure 4C:
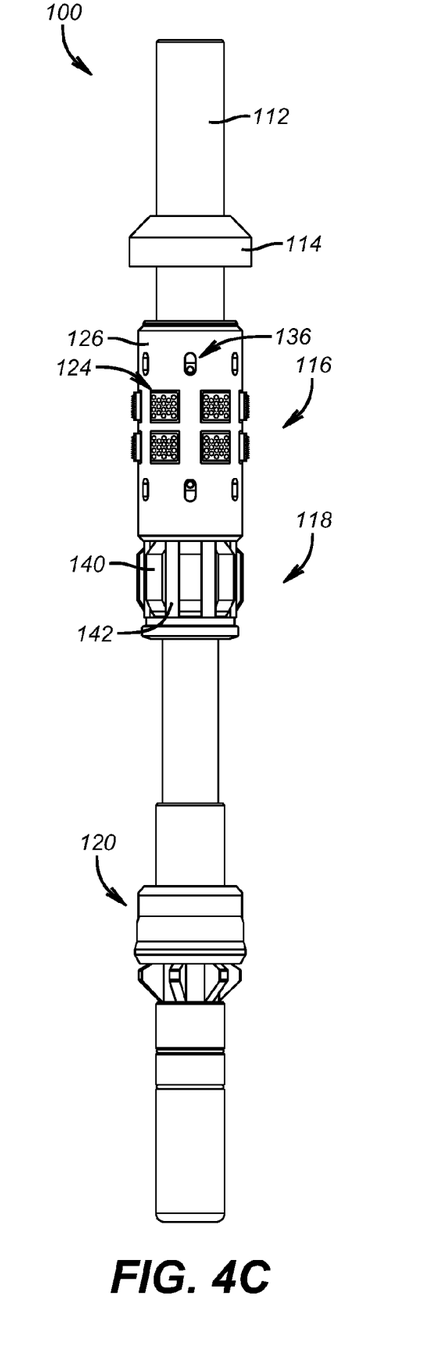
FIG. 4C is an elevation of the casing spear of FIG. 4A in a set position.
Figure 4D:
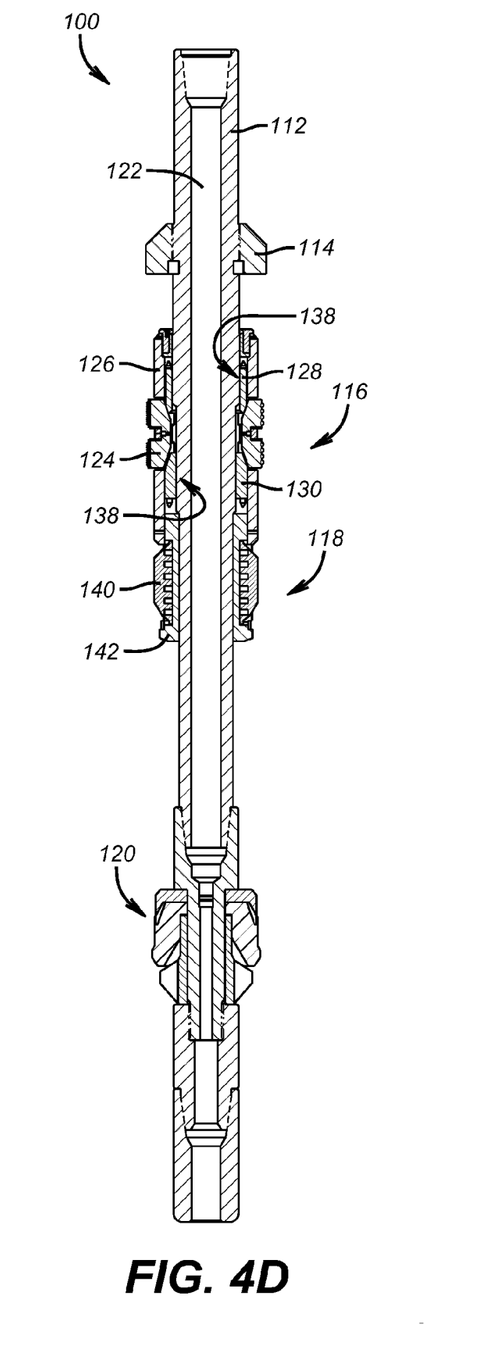
FIG. 4D is a cross-sectional view of the casing spear of FIG. 4A, in the set position.

The slip assembly 116 may include a plurality of slips 124, an outer housing 126, an upper wedge 128 and a lower wedge 130 (FIGS. 4B and 4D). The outer housing 126 may be rotatably coupled to the mandrel 112 and each of the slips 124 may be positioned within the outer housing 126 and portions of the slips 124 may extend through apertures in the outer housing 126. The upper wedge 128 and the lower wedge 130 may be positioned radially between the mandrel 112 and the outer housing 126. The upper wedge 128 may be positioned axially above the slips 124 and the lower wedge 130 may be positioned axially below the slips 124. The slips 124 may include surfaces that are angled (e.g., at an acute angle) relative to a longitudinal axis of the mandrel 112 and the upper and lower wedges 128 and 130 may include angled surfaces adjacent respective angled surfaces of the slips 124 and oriented at a supplemental angle thereto. The outer surfaces 132 of the slips comprise gripping structures. Such gripping structures may comprise, by way of non-limiting example, machined teeth, wickers, crushed tungsten carbide, tungsten carbide inserts 134 in the form of bricks, buttons or discs, superabrasive elements such as natural or polycrystalline diamond, or a combination thereof. In one embodiment, such as shown in FIG. 5, the gripping structures comprise tungsten carbide inserts 134 in the form of buttons having four projecting, pyramidal points. In additional embodiments, the gripping structures may be wickers 135, 137, such as shown in FIGS. 6 and 7, which may be oriented in an axial direction (FIG. 6), a circumferential direction, another direction or a combination thereof (FIG. 7).

A linear slide 136 (FIGS. 4A and 4C) may prevent or limit circumferential movement of the outer housing 126 relative to each of the upper wedge 128 and the lower wedge 130. The linear slide 136 may allow relative linear motion between the outer housing 126 and each of the upper wedge 128 and the lower wedge 130 in an axial direction. For example, the outer housing 126 may include slots positioned over each of the upper wedge 128 and the lower wedge 130, and corresponding pins (e.g., cap screws) may extend into the slots, respectively. The pins may be coupled to the upper wedge 128 and the lower wedge 130, respectively, and limit the respective range of motion of the upper wedge 128 and the lower wedge 130.

Each of the upper wedge 128 and the lower wedge 130 may include a threaded region 138 mated with corresponding threads on the outer surface of the mandrel 112. Additionally, the outer housing 126 may be fixedly coupled to the drag block assembly 118. The drag block assembly 118 may include a plurality of drag blocks 140 circumferentially distributed within a frame 142, and the drag blocks 140 may be biased radially outward, such as by helical compression springs.

In a run-in position, such as shown in FIGS. 4A and 4B, the casing spear 100 may be inserted into a casing joint 50, which may be made up with another casing joint 52 already positioned in a well bore similarly as to described with reference to FIG. 3, and the casing spear 100 may be rotated, such as in a right-hand direction (i.e., clockwise looking down into the borehole). Friction between the drag blocks 140 and an interior surface of the casing may be used to apply torque to the drag block assembly 118. The torque acting on the drag block assembly 118 will also act on outer housing 126, which is coupled to the drag block assembly 118, as well as the slips 124, the upper wedge 128 and the lower wedge 130. The torque on the upper wedge 128 and the lower wedge 138 will cause the upper wedge 128 and the lower wedge 130 to rotate relative to the mandrel 112 at the threaded connections therebetween. Upon rotation, the threads will guide the upper wedge 128 downward, toward the lower wedge 130, and will guide the lower wedge 130 upwards, toward the upper wedge 128.

As the upper wedge 128 and the lower wedge 130 are urged together, the angled surfaces of the upper wedge 128 and the lower wedge 130 will be forced against the angled surfaces of the slips 124. The general wedge-like shapes of the slips 124 and upper and lower wedges 128 and 130 will cause the slips 124 to be urged radially outwards through the apertures in the outer housing 126 as the upper wedge 128 and the lower wedge 130 are urged together. When the slips 124 have been urged sufficiently radially outwards to a set position, such as shown in FIGS. 4C and 4D, the gripping structures of the slips 124 may grip the inner surface of the casing, and the torsion applied to the mandrel 112 may be applied to the casing through the slips 124. Additionally, upon the slips 124 contacting the inner surface of the casing, the torsion applied to the slips 124 may cause the slip assembly 116 to rotate relative to the mandrel 112, or at least provide torsion between the slip assembly 116 and the mandrel 112, which will provide additional force to urge the upper and lower wedges 128 and 130 together as the mandrel 112 is rotated. In view of this, as the torque applied to the slips 124 is increased, the axial force applied by the slips 124 to the inner surface of the casing may be increased.

To remove the casing spear 100, the mandrel 112 may be rotated in the opposite direction, such as in a left-hand direction (i.e., counter-clockwise looking down into the borehole), which may cause the lower wedge 130 to be forced downward, away from the upper wedge 128. As the lower wedge 130 is moved longitudinally away from the upper wedge 128, the slips 124 may retract axially toward the mandrel 112 and the casing spear 100 may be removed from the casing.

In additional embodiments, the upper wedge 128 may be fixed relative to the mandrel 112 and the lower wedge 130 and the slips 124 may be urged toward the upper wedge 128 upon rotation of the mandrel 112 and the lower wedge 130 and the slips 124 may be urged away from the upper wedge 128 upon reverse rotation of the mandrel 112. In yet further embodiments, the lower wedge 130 may be fixed relative to the mandrel 112 and the upper wedge 128 and the slips 124 may be urged toward the lower wedge 130 upon rotation of the mandrel 112 and the upper wedge 128 and the slips 124 may be urged away from the lower wedge 130 upon reverse rotation of the mandrel 112.

Figure 8A:
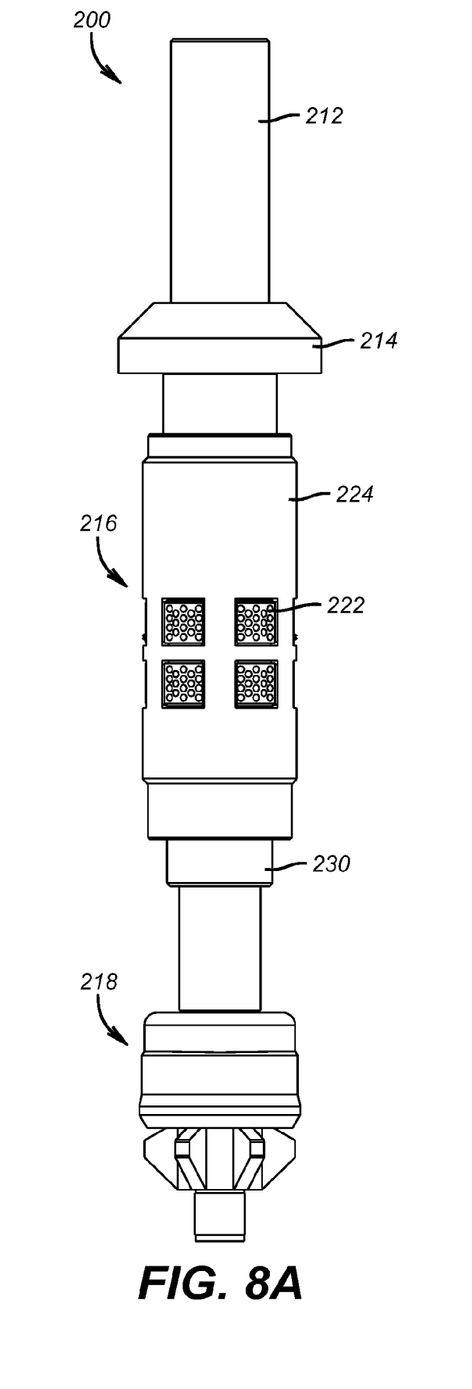
FIG. 8A is an elevation of a casing spear, according to an additional embodiment of the present invention, in a run-in position.
Figure 8B:
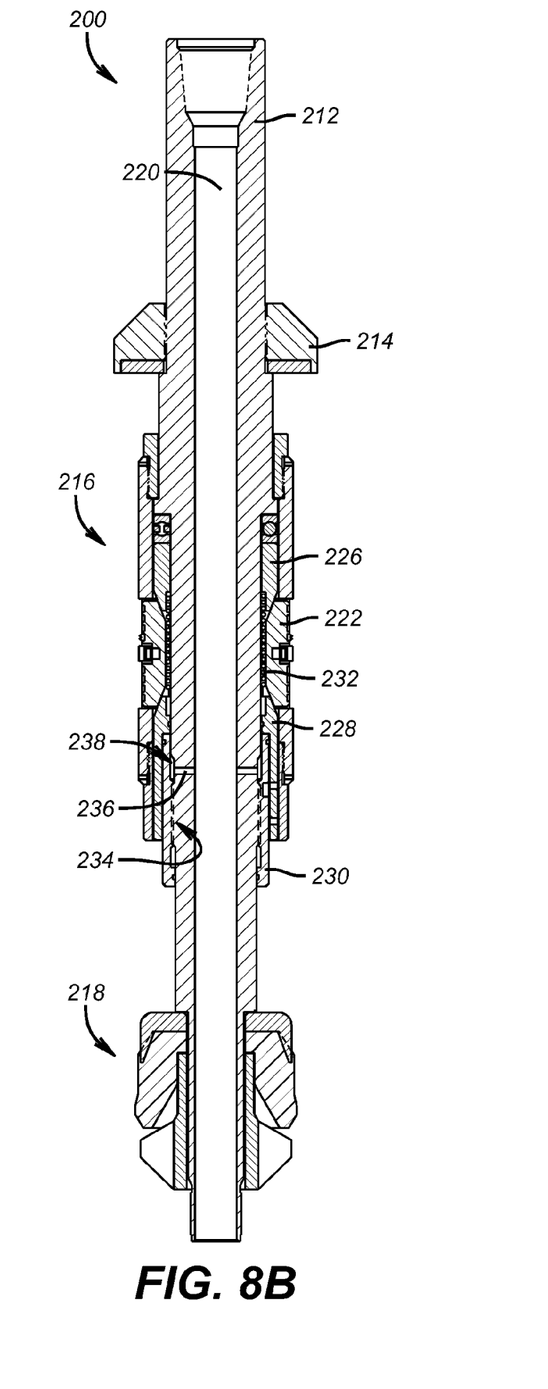
FIG. 8B is a cross-sectional view of the casing spear of FIG. 8A, in the run in position.
Figure 8C:
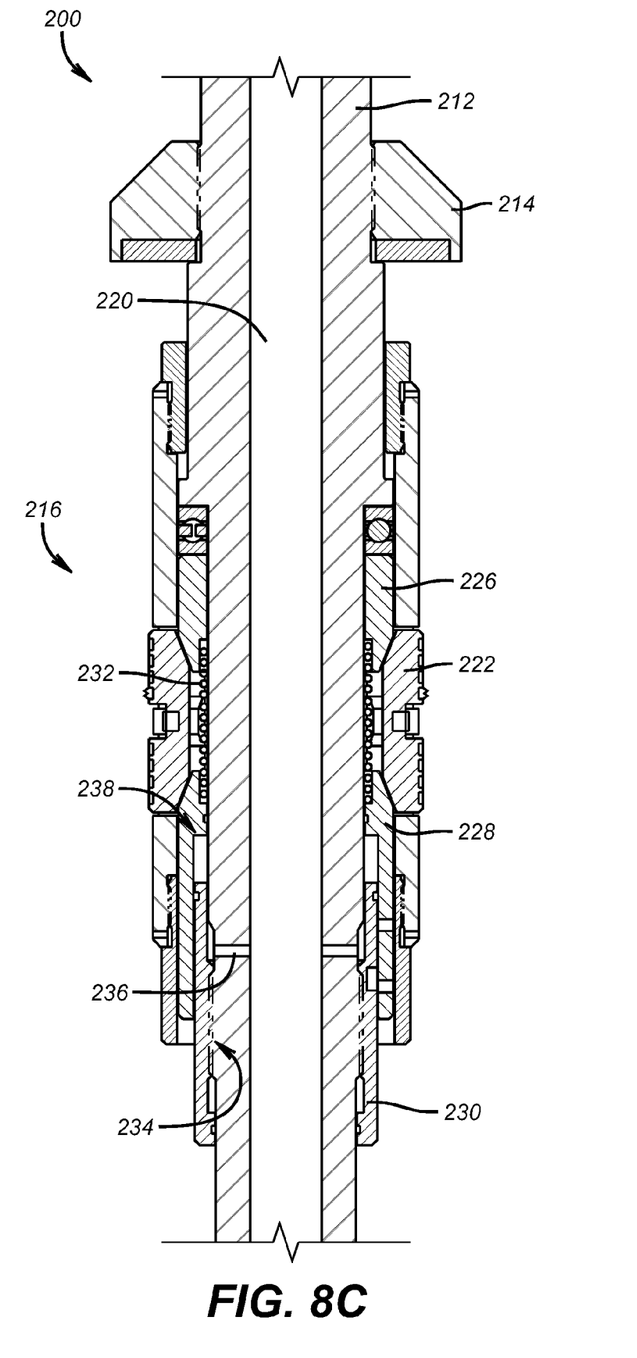
FIG. 8C is a cross-sectional detail view of the casing spear of FIG. 8A, in a set position.

In an additional embodiment, such as shown in FIGS. 8A-8C, a casing spear 200 may comprise a mandrel 212, a circumferential stop collar 214, a slip assembly 216, and a cup type packer 218. The mandrel 212 may include a longitudinal fluid passage 220 (FIGS. 8B and 8C) extending therethrough and the mandrel 212 may be coupled to the cup type packer 218, as shown. Optionally, the mandrel 212 may be coupled to an assembly that includes a cup type packer, such as by a threaded connection, as shown in FIG. 3. Additionally the circumferential stop collar 214 may be coupled to the mandrel 212 such that the stop collar 214 may be prevented from axial movement relative to the mandrel 212.

The slip assembly 216 may include a plurality of slips 222, an outer housing 224, an upper wedge 226, a lower wedge 228 (FIGS. 8B and 8C), and a lock ring 230. The outer housing 224 may be rotatably coupled to the mandrel 212 and each of the slips 222 may be positioned within the outer housing 224 and portions of the slips 222 may extend through apertures in the outer housing 224. The upper wedge 226 and the lower wedge 228 may be positioned radially between the mandrel 212 and the outer housing 224. The upper wedge 226 may be positioned axially above the slips 222 and the lower wedge 228 may be positioned axially below the slips 222. The slips 222 may include surfaces that are angled relative to the longitudinal axis of the mandrel 212 and the upper and lower wedges 226 and 228 may include angled surfaces adjacent respective angled surfaces of the slips 222 and oriented at a supplemental angle thereto. The outer surfaces of the slips 222 may comprise gripping structures. Such gripping structures may comprise, by way of non-limiting example, machined teeth, wickers, crushed tungsten carbide, tungsten carbide inserts in the form of bricks, buttons or discs, superabrasive elements such as natural or polycrystalline diamond, or a combination thereof. In one embodiment, such as shown in FIG. 5, the gripping structures comprise tungsten carbide inserts in the form of buttons having four projecting, pyramidal points. In additional embodiments, the gripping structures may be wickers, such as shown in FIGS. 6 and 7, which may be oriented in an axial direction, a circumferential direction, another direction or a combination thereof.

A helical compression spring 232 (FIGS. 8B and 8C) may be positioned between the upper wedge 226 and the lower wedge 228, and the lock ring 230 may be positioned below the lower wedge 228. The lock ring 230 may include a threaded region 234 mated with corresponding threads on the outer surface of the mandrel 212. One or more fluid paths 236 may provide fluid communication between the longitudinal fluid passage 220 of the mandrel 212 and a fluid space 238 between the lock ring 230 and the lower wedge 228.

In a run-in position, such as shown in FIGS. 8A and 8B, the casing spear 200 may be inserted into a casing joint 50, which may be made up with another casing joint 52 positioned in a well bore similarly as to described with reference to FIG. 3. Via the longitudinal passage 220 of the mandrel 212 drilling fluid may be directed through the one or more fluid paths 236 into the fluid space 238 between the lock ring 230 and the lower wedge 228, which may cause the lower wedge 228 to be pushed longitudinally upward, toward the slips 222 and the upper wedge 226.

As the lower wedge 228 is urged upward, toward the upper wedge 226, the angled surfaces of the upper wedge 226 and the lower wedge 228 will be forced against the angled surfaces of the slips 222. The general wedge-shapes of the slips 222 and upper and lower wedges 226 and 228 will cause the slips 222 to be urged radially outwards as the lower wedge 228 moves upwards, toward the upper wedge 226. When the slips 222 have been urged sufficiently radially outwards to a set position, as shown in FIG. 8C, the gripping structures of the slips 222 may grip the inner surface of the casing, and the rotational force applied to the mandrel 212 may be applied to the casing through the slips 222.

Initially, the slip assembly 216 may rotate relative to the mandrel 212 as the slips 222 grip the inner surface of the casing and the mandrel 212 is rotated, such as in a right hand direction (i.e., clockwise looking down into the borehole). As the slip assembly 216 rotates relative to the mandrel 212, the locking ring 230 may also rotate relative to the mandrel 212 and the threaded interface between the locking ring 230 and the mandrel 212 may cause the locking ring 230 to move longitudinally upwards, toward the lower wedge 228. As the locking ring 230 is forced longitudinally upward, toward the lower wedge 228, the fluid space 238 between the locking ring 230 and the lower wedge 228 may become smaller and the fluid may be expelled from the fluid space 238 as the locking ring 230 contacts the lower wedge 228. Upon being directed toward and contacting the lower wedge 228, the locking ring 230 will provide additional force to the lower wedge 228 as torque is applied to the slips 222 by the casing as the mandrel 212 is rotated and will also prevent the slip assembly 216 from rotating relative to the mandrel 212. In view of this, as torque applied to the slips 222 is increased, the axial force applied by the slips 222 to the inner surface of the casing may be increased and the casing spear 200 may effectively rotate the casing.

To remove the casing spear 200, the mandrel 212 may be rotated in the opposite direction, such as in a left-hand direction (i.e., counter-clockwise looking down into the borehole), which may cause the locking ring 230 to rotate relative to the mandrel 212 and be forced axially downward, away from the slips 222. Additionally, the pumping of drilling fluid may be ceased, or the pressure reduced, and the helical compression spring 232 may force the lower wedge 228 axially downward, toward the locking ring 230 and away from the upper wedge 226 and the slips 222. As the lower wedge 228 is moved axially away from the upper wedge 226, the slips 222 may retract axially toward the mandrel 212 to the run-in position, and the casing spear 200 may be removed from the casing.

Figure 9A:
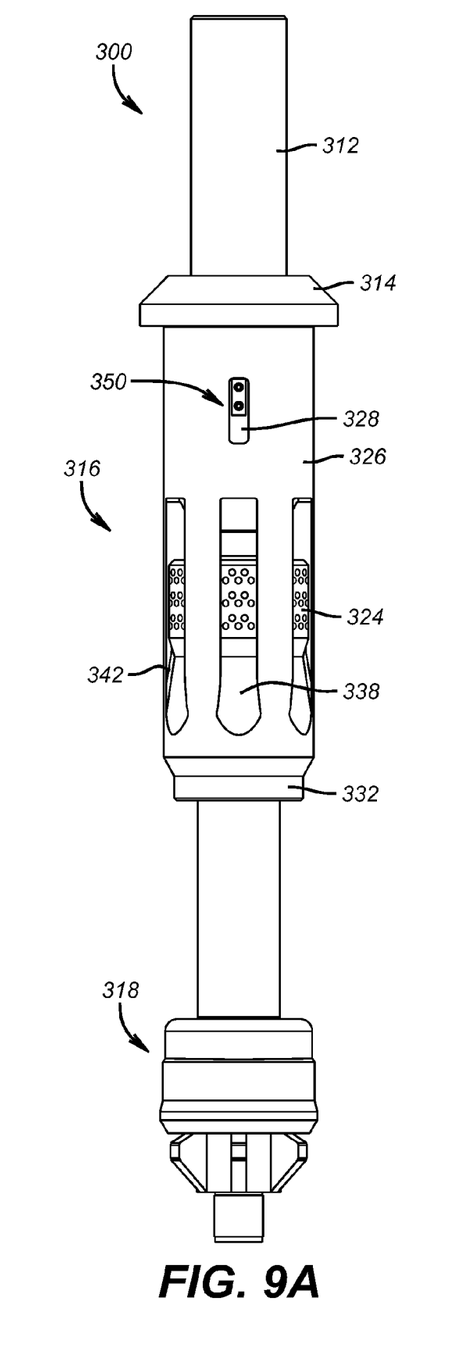
FIG. 9A is an elevation of a casing spear, according to an additional embodiment of the present invention, in a run-in position.
Figure 9B:
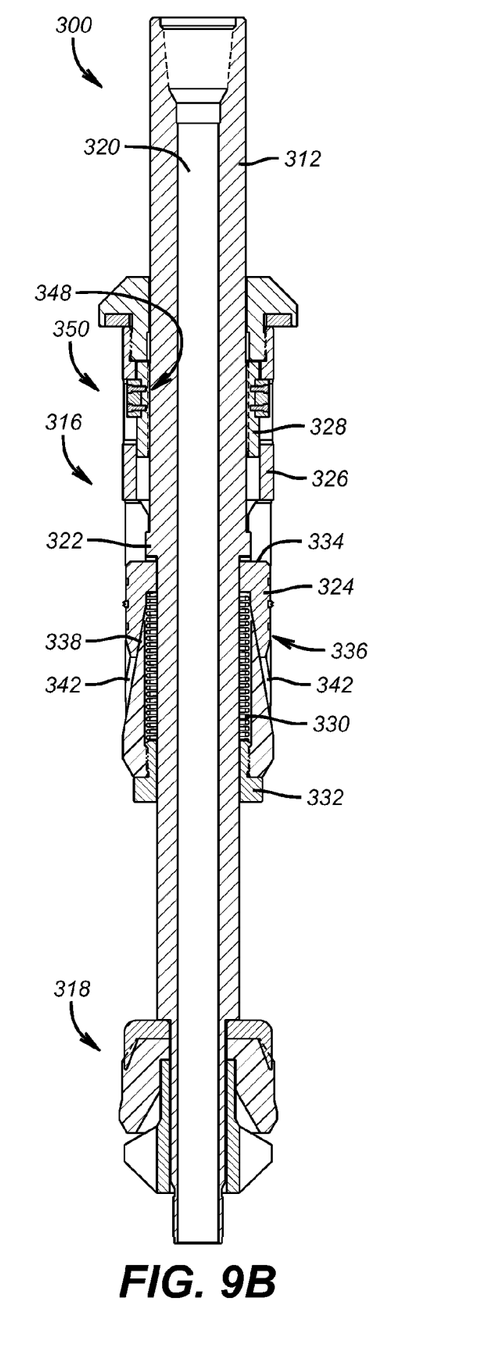
FIG. 9B is a cross-sectional view of the casing spear of FIG. 9A, in the run in position.
Figure 9C:
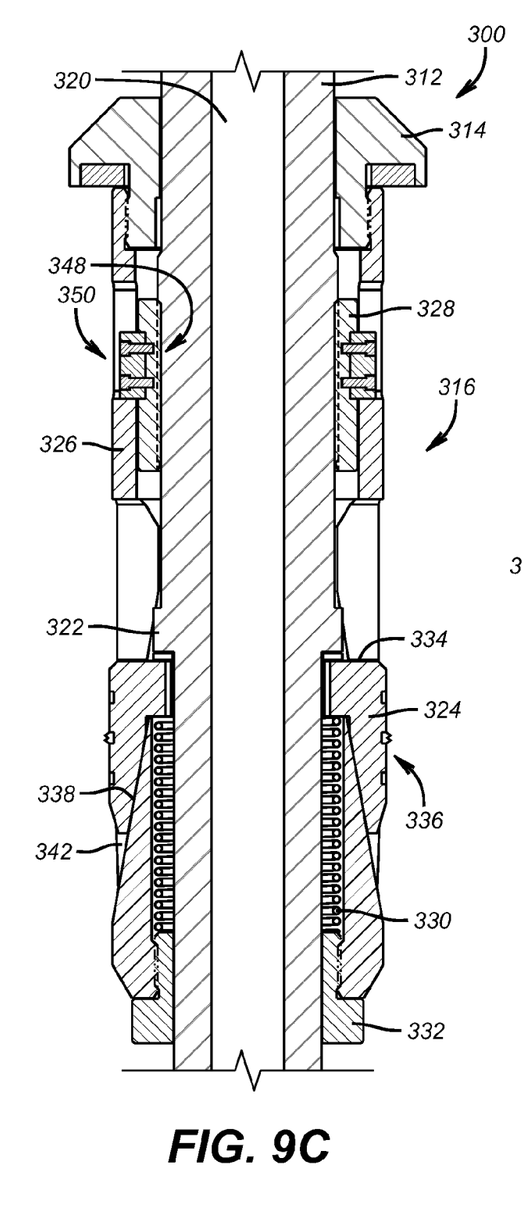
FIG. 9C is a cross-sectional detail view of the casing spear of FIG. 9A, in a set position.

In an additional embodiment, such as shown in FIGS. 9A-9C, a casing spear 300 may comprise a mandrel 312, a circumferential stop collar 314, a slip assembly 316, and a cup type packer 318. The mandrel 312 may include a longitudinal fluid passage 320 (FIGS. 9B and 9C) extending therethrough and the mandrel 312 may be coupled to the cup type packer 318, as shown. Additionally, the mandrel 312 may include a stop ring 322 (FIGS. 9B and 9C) extending radially outward therefrom.

Figure 10:
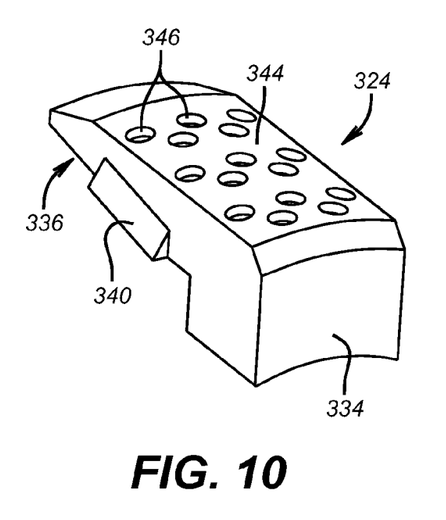
FIG. 10 is an isometric view of a slip for a casing spear, such as shown in FIG. 9A.

The circumferential stop collar 314 may be coupled to the slip assembly 316, which may include a plurality of slips 324, an outer housing 326, a locking ring 328, a biasing member 330 (FIGS. 9B and 9C) and a retaining ring 332. The outer housing 326 may be positioned on the mandrel 312, over the stop ring 322 and each of the slips 324 may be positioned within the outer housing 326 and portions of the slips 324 may extend through corresponding apertures in the outer housing 326. Each of the slips 324 may include an end surface 334 abutting the stop ring 322 of the mandrel 312 and an opposing wedged end 336 overlying an angled surface 338 (i.e., at an acute angle relative to the longitudinal axis of the mandrel) of the outer housing 326. Each slip 324 may additionally include a set of protrusions 340 (FIG. 10) corresponding to tracks 342 in the outer housing 326, which may limit movement of the slips 324 relative to the outer housing 326 to a substantially linear motion. The outer surfaces 344 of the slips may comprise gripping structures. Such gripping structures may comprise, by way of non-limiting example, machined teeth, wickers, crushed tungsten carbide, tungsten carbide inserts in the form of bricks, buttons or discs (which may be inserted into pockets 346), superabrasive elements such as natural or polycrystalline diamond, or a combination thereof.

The locking ring 328 may be positioned within the outer housing 326, between the outer housing 326 and the mandrel 312. The locking ring 328 may include a threaded region 348 mating with a corresponding threaded region of the mandrel 312. A linear slide 350 may limit motion of the locking ring 328 relative to the outer housing 326 to linear motion in an axial direction. For example, the outer housing 326 may include slots positioned over the locking ring 328, and corresponding pins (e.g., cap screws), or other axially protruding features, coupled to the locking ring 328 may extend into the slots, respectively.

The biasing member 330, such as a helical compression spring, as shown, may be contained within the outer housing 326 and held against the slips 324 by the retaining ring 332, which may be coupled to the outer housing 326. In view of this, the biasing member 330 may bias the slips 324 towards the stop ring 322 of the mandrel 312.

In a run-in position, such as shown in FIGS. 9A and 9B, the casing spear 300 may be inserted into a casing, which may be made up with another casing positioned in a well bore similarly as described with reference to FIG. 3, and the top of the casing may come into contact with the circumferential stop collar 314. As set down weight is applied to the casing, the casing may apply an opposing upward force on the circumferential stop collar 314 and prevent the circumferential stop collar 314, and attached outer housing 326 of the slip assembly 316, from moving axially downward as the mandrel 312 continues to move axially downward relative to the circumferential stop collar 314, the outer housing 326 of the slip assembly 316, and the casing. The stop ring 322 of the mandrel 312 may apply an axially downward force to the slips 324, which may compress the biasing member 330 and may cause the slips 324 to move axially downward relative to the outer housing 326 of the slip assembly 316. As the slips 324 are moved axially downward relative to the outer housing 326 the protrusions 340 of the slips 324 may move linearly along the tracks 342 of the outer housing 326 and the wedged ends 336 of the slips 324 may move along the angled surfaces 338 of the outer housing 326, which will cause the slips 324 to be urged radially outward to a set position, as shown in FIG. 9C, and into contact with an inner surface of the casing. The mandrel 312 may then be rotated, such as in a right hand direction (i.e., clockwise looking down into the borehole), and the contact between the slips 324 and the inner surface of the casing may cause the mandrel 312 to rotate relative to the slip assembly 316 (optionally the mandrel 312 may also be rotated prior to the slips 324 contacting the inner surface of the casing). As the mandrel 312 rotates relative to the slip assembly 316, the threaded connection between the locking ring 328 and the mandrel 312 may cause the locking ring 328 to be urged axially upward relative to the mandrel 312, and the outer housing 316 and circumferential stop 314 of the slip assembly 316. As the locking ring 328 moves axially upward it may contact either the outer housing 326 and/or the circumferential stop ring 314 and apply an axially upward force on the outer housing 326. After the locking ring 328 is moved axially upward and applies a force to the outer housing 326, the outer housing 326 may be prevented from any substantial rotation relative to the mandrel 312. In view of this, the torsion applied to the slips 324 by the casing (countering the rotational force applied by the mandrel 312) may cause the locking ring 328 to apply additional force to the outer housing 326, which may, in turn, apply additional force to urge the slips 324 radially outward to grip the casing. In view of this, as torque applied to the slips 324 is increased, the axial force applied by the slips 324 to the inner surface of the casing may be increased and the casing spear 300 may effectively rotate the casing.

To remove the casing spear 300 from the casing, at least a portion of the set down weight may be taken off of the casing spear 300 and the mandrel 312 may be rotated in the opposite direction, such as in a left hand direction (i.e., counter-clockwise looking down into the borehole). The reverse rotation of the mandrel 312 may cause the slip assembly 316, including the locking ring 328 to rotate in the opposite direction relative to the mandrel 312. The threaded connection between the locking ring 328 and the mandrel 312 may cause the locking ring 328 to be urged axially downward. As the locking ring 328 is urged downward, the force holding the outer housing 326 may be alleviated and the outer housing may move axially downward relative to the mandrel 312. Meanwhile, the biasing member 330 may continue to urge the slips 324 against the stop ring 322 as the outer housing 326 moves axially downward and the slips 324 may be urged axially inward, away from the inner surface of the casing to the run-in position. After the slips 324 have retracted axially toward the mandrel 312, away from the inner surface of the casing, the casing spear 300 may be removed from the casing.

While particular embodiments of the invention have been shown and described, numerous variations and alternate embodiments will occur to those skilled in the art. Accordingly, it is intended that the invention only be limited in terms of the appended claims and their legal equivalents.

We claim:

1. A tubular spear for axially and rotationally moving at least one tubular to a subterranean location, comprising:
    a mandrel having a flow passage therethrough;
    a gripping assembly mounted over said mandrel and further comprising:
        a housing assembly;
        a plurality of slips supported by said housing assembly for relative longitudinal movement of said slips that results in radial movement of said slips toward said tubular;
        a drag block assembly for contacting the tubular to retain a portion of said housing assembly when said mandrel is rotated for at least one turn, said mandrel rotation creating said relative longitudinal slip movement that moves said slips to engage the tubular for torque transmission to the tubular;
    said slips contact each other to form a ring shape.

2. The spear of claim 1, wherein:
    said slips comprise edge dovetail connections.

3. The spear of claim 2, wherein:
    said housing assembly comprises first and second spaced support rings connected respectively to every other of said slips such that relative movement of said support rings toward each other extends said slips and relative movement of said support rings away from each other retracts said slips.

4. The spear of claim 3, wherein:
    at least one said support ring is connected to said mandrel with a thread.

5. The spear of claim 4, wherein:
    one said support ring is connected to said mandrel with a thread and the other is mounted for free relative rotation with respect to said mandrel such that mandrel rotation advances one said support ring axially toward or away from the other said support ring.

6. The spear of claim 4, wherein:
    both said support rings are connected to said mandrel with a thread;

said thread connecting one support ring to said mandrel is opposite hand to said thread connecting the other said support ring to said mandrel.

7. The spear of claim 4, further comprising:
a stop collar on said mandrel to position said slips within the tubular when landed on the tubular.

8. The spear of claim 4, further comprising:
at least one exterior seal on said mandrel against the tubular to prevent flow between said mandrel and the tubular coming from the subterranean location.

9. The spear of claim 8, wherein:
said seal is rotatably mounted to allow said mandrel to turn while said seal remains stationary.

10. The spear of claim 9, wherein:
said seal comprises a cup seal having an open end oriented toward said subterranean location.

11. The spear of claim 8, wherein:
said drag block assembly comprises a plurality of spring loaded blocks mounted about the periphery of said housing assembly;
said slips comprise external wickers and a grip enhancing feature.

12. The spear of claim 8, wherein:
said slips comprise wickers axially aligned with an axis of said mandrel for enhanced grip when torque is applied to said mandrel with said slips engaging the tubular.

13. A tubular spear for axially and rotationally moving at least one tubular to a subterranean location, comprising:
a mandrel having a flow passage therethrough;
a gripping assembly mounted over said mandrel and further comprising:
a housing assembly;
a plurality of slips supported by said housing assembly said slips having longitudinally oriented wickers in general alignment with an axis of said mandrel for gripping the tubular to transmit torque delivered from said mandrel;
a drag block assembly for contacting the tubular to retain a portion of said housing assembly when said mandrel is rotated for at least one turn, said mandrel rotation axially advancing at least one cone in said housing assembly with respect to said slips to engage said slips to the tubular.

14. The spear of claim 13, wherein:
said drag block assembly comprises a stop collar mounted adjacent a top end of said housing to engage the tubular.

15. The spear of claim 13, wherein:
said drag block assembly comprises a plurality of spring loaded blocks mounted adjacent a lower end of said housing assembly.

16. The spear of claim 14, wherein:
said slip is driven axially with respect to said cone by mandrel rotation;
said cone is spring biased toward said slip.

17. The spear of claim 16, wherein:
said stop collar prevents rotation of said housing assembly when said stop collar lands on the tubular;
said slips are connected to said mandrel with a thread such that rotation of said mandrel with weight on said stop collar axially advances said slips toward said cone with said bias on said cone in an axial direction retaining said slips extended toward the tubular.

18. The spear of claim 13, wherein:
said mandrel further comprises at least one peripheral seal mounted thereto to permit relative rotation of said mandrel relative to said seal that is in contact with the tubular.

19. The spear of claim 18, wherein:
said seal comprises a cup shape with an open end oriented toward the subterranean location.

20. The spear of claim 13, wherein:
said at least one cone comprises of a plurality of cones with one on each of opposed sides of said slips;
at least one of said cones moving axially toward or away from another said cone on an opposite side of said slips in response to mandrel rotation.

21. The spear of claim 20, wherein:
at least one said cone is connected to said mandrel with a thread.

22. The spear of claim 21, wherein:
at least one said cone is axially retained to said housing assembly.

23. The spear of claim 21, wherein:
each said cones are retained to said mandrel with respective threads that are opposite hand.

24. The spear of claim 13, wherein:
said mandrel comprises a stop collar that lands on the tubular to place said slips at a predetermined location;
said drag assembly comprises a plurality of blocks that are radially biased toward the tubular;
said mandrel comprises a peripheral seal rotatably mounted to said mandrel for contact with the surrounding tubular when said stop collar is landed on the tubular.

25. The spear of claim 24, wherein:
said slips further comprise a hardened material adjacent said wickers to increase grip as torque is applied from said mandrel with said wickers against the tubular.

26. A tubular spear for axially and rotationally moving at least one tubular to a subterranean location, comprising:
a mandrel having a flow passage therethrough;
a gripping assembly mounted over said mandrel and further comprising:
a housing assembly;
a plurality of slips supported by said housing assembly;
a port from said passage to a cone, said cone responsive to pressure in said passage, to move said slips radially toward the tubular;
a lock ring to selectively support said cone when said slips contact the tubular and pressure in said passage is removed;
rotation of said mandrel, with said slips against the tubular, axially moves said lock ring against said cone.

27. The spear of claim 26, wherein:
said lock ring is connected to said mandrel with a thread.

28. The spear of claim 27, wherein:
said slips having longitudinally oriented wickers in general alignment with an axis of said mandrel for gripping the tubular to transmit torque delivered from said mandrel.

29. The spear of claim 28, wherein:
said mandrel further comprises a rotatably mounted peripheral seal to engage the tubular to prevent flow from the subterranean location therebetween;
said mandrel further comprises a stop collar to locate said slips at a predetermined location in the tubular.

30. The spear of claim 29, wherein:
said at least one cone comprises spaced apart cones on opposed sides of said slips that are biased away from each other;
pressure in said passage drives one of said cones against said bias while the other of said cones is axially supported by said mandrel.

* * * * *